United States Patent
Ohkubo et al.

(10) Patent No.: US 10,975,013 B2
(45) Date of Patent: Apr. 13, 2021

(54) METHOD FOR PRODUCING VANILLIN

(71) Applicant: T. HASEGAWA CO., LTD., Tokyo (JP)

(72) Inventors: Yasutaka Ohkubo, Kawasaki (JP); Yusuke Fukushima, Kawasaki (JP); Yu Kinjo, Fukaya (JP)

(73) Assignee: T. Hasegawa Co., Ltd, Tokyo (JP)

( * ) Notice: Subject to any disclaimer, the term of this patent is extended or adjusted under 35 U.S.C. 154(b) by 0 days.

(21) Appl. No.: 16/966,439

(22) PCT Filed: Jan. 24, 2019

(86) PCT No.: PCT/JP2019/002274
§ 371 (c)(1),
(2) Date: Jul. 30, 2020

(87) PCT Pub. No.: WO2019/155899
PCT Pub. Date: Aug. 15, 2019

(65) Prior Publication Data
US 2021/0040024 A1 Feb. 11, 2021

(30) Foreign Application Priority Data

Feb. 9, 2018 (JP) ................................. 2018-022271

(51) Int. Cl.
*C07C 45/83* (2006.01)
*C07C 47/58* (2006.01)

(52) U.S. Cl.
CPC .............. *C07C 47/58* (2013.01); *C07C 45/83* (2013.01)

(58) Field of Classification Search
CPC ....................................................... C07C 45/83
See application file for complete search history.

(56) References Cited

U.S. PATENT DOCUMENTS

| 2,506,540 | A | 5/1950 | Bryan |
| 5,510,006 | A | 4/1996 | Jones et al. |

FOREIGN PATENT DOCUMENTS

| JP | 2006-83117 A | 3/2006 |
| JP | 2015-507615 A | 3/2015 |
| JP | 2016-508482 A | 3/2016 |

OTHER PUBLICATIONS

International Search Report dated Apr. 16, 2019, issued in corresponding Application PCT/JP2019/002274, 5 pages.

*Primary Examiner* — Sikarl A Witherspoon
(74) *Attorney, Agent, or Firm* — Christensen O'Connor Johnson Kindness PLLC

(57) ABSTRACT

The present invention relates to a method for producing vanillin, including the steps of: (A) distilling a solution containing crude vanillin and an aliphatic dicarboxylic acid dialkyl ester to obtain a vanillin solution; and (B) subjecting the vanillin solution to anti-solvent crystallization. The method for producing vanillin according to the present invention enables production of high-purity vanillin with industrially sufficient efficiency without use of a special apparatus.

6 Claims, No Drawings

METHOD FOR PRODUCING VANILLIN

TECHNICAL FIELD

The present invention relates to a method for producing vanillin.

BACKGROUND ART

Vanillin is an aroma component contained in vanilla beans, and is used as a flavor and fragrance for food products, cosmetic products and the like. As methods for artificially synthesizing vanillin, roughly two methods have been heretofore known. One is synthesis based on chemical synthetic methods and the other is synthesis based on biochemical methods. For any of these methods, however, produced vanillin is accompanied by involatile impurities as by-products.

While crystallization from a water-alcohol system is known as a method for removing impurities contained in produced vanillin, a substance hardly soluble in a solvent, such as vanillic acid which is an oxidation product of vanillin and divanillin which is a dimer of vanillin, is difficult to sufficiently remove by such crystallization. While distillation purification is known as a method for effectively removing such impurities, vanillin has a high melting point of 81 to 83° C., so that a special apparatus for operating the vanillin in a liquid state at a high temperature or for performing crystal distillation is necessary. From this viewpoint, methods have been proposed in which vanillin is dissolved in a solvent, and extracted together with the solvent to distill the vanillin in a liquid form (see, for example, Patent Literatures 1 and 2).

CITATION LIST

Patent Literature

Patent Literature 1: U.S. Pat. No. 2,506,540
Patent Literature 2: U.S. Pat. No. 5,510,006

SUMMARY OF INVENTION

Technical Problem

However, the methods described in Patent Literatures 1 and 2 have problems in terms of efficiency in industrially practical use because some equipment is required for eliminating inconveniences resulting from an excessively high or low solubility of vanillin in a solvent. Thus, conventional arts do not enable distillation purification of vanillin with industrially sufficient efficiency without use of a special apparatus.

The present invention has been made in view of the situations described above, and an object of the present invention is to provide a method for producing high-purity vanillin with industrially sufficient efficiency without use of a special apparatus.

Solution to Problem

The present inventors have extensively conducted studies, and resultantly found that the above-described problems can be solved by anti-solvent crystallization using a predetermined material, leading to completion of the present invention.

That is, the present invention includes the following aspects.

[1] A method for producing vanillin, including the steps of:
  (A) distilling a solution containing crude vanillin and an aliphatic dicarboxylic acid dialkyl ester to obtain a vanillin solution; and
  (B) subjecting the vanillin solution to anti-solvent crystallization.

[2] The method for producing vanillin according to [1], wherein a hydrocarbon solvent is used in the anti-solvent crystallization.

[3] The method for producing vanillin according to [1] or [2], wherein the aliphatic dicarboxylic acid dialkyl ester is selected from the group consisting of dibutyl maleate, dibutyl succinate, diethyl sebacate, diisobutyl adipate and a mixture thereof.

[4] The method for producing vanillin according to [2] or [3], wherein the hydrocarbon solvent is selected from the group consisting of n-hexane, n-heptane, cyclohexane and a mixture thereof. [5] The method for producing vanillin according to any one of [2] to [4], further including the following steps:
  (C) separating the aliphatic dicarboxylic acid dialkyl ester and the hydrocarbon solvent from a crystallization mother liquor from step (B); and
  (D) recycling the aliphatic dicarboxylic acid dialkyl ester and/or the hydrocarbon solvent obtained in step (C).

[6] A composition containing:
  vanillin in an amount of 97.0 mass % or more and 99.99 mass % or less;
  an aliphatic dicarboxylic acid dialkyl ester in an amount of 0.001 mass % or more and 1 mass % or less; and
  a hydrocarbon solvent in an amount of 0.001 mass % or more and 1 mass % or less.

Advantageous Effects of Invention

According to the present invention, it is possible to produce high-purity vanillin with industrially sufficient efficiency without use of a special apparatus.

DESCRIPTION OF EMBODIMENTS

An embodiment for carrying out the present invention (hereinafter, simply referred to as "the present embodiment") will be described in detail below. The present embodiment is illustrative for explaining the present invention, and the present invention is not limited solely to the following embodiment.

[Method for Producing Vanillin]

The method for producing vanillin according to the present embodiment includes steps of: (A) distilling a solution containing crude vanillin and an aliphatic dicarboxylic acid dialkyl ester to obtain a vanillin solution; and (B) subjecting the vanillin solution to anti-solvent crystallization. The method for producing vanillin according to the present embodiment enables high-purity vanillin (hereinafter, also referred to as "purified vanillin") to be obtained with industrially sufficient efficiency without use of a special apparatus by performing anti-solvent crystallization using a predetermined material as described above.

The purified vanillin as used herein means a vanillin crystal obtained by synthesis, which has a vanillin content of 97.0 mass % or more. From the viewpoint of quality in food applications, the vanillin content is preferably 99.0 mass % or more, more preferably 99.9 mass % or more. From the same viewpoint, the purified vanillin is particularly preferably one that complies with the "Vanillin" section in Japan's Specifications and Standards for Food Additives and the U.S. Standard of the Food Chemicals Codex. More specifically, the purified vanillin is especially preferably one that is an acicular crystal or powder in terms of characteristics, and white or light yellow in terms of a color tone and that has a purity of 97.0% or more, a melting point of 81 to 83° C., a loss on drying of 0.5% or less, a residue on ignition of 0.05% or less, a heavy metal content of 10 ppm or less and an arsenic content of 4 ppm or less.

(Step (A))

In step (A), a solution containing crude vanillin and an aliphatic dicarboxylic acid dialkyl ester is prepared, and the solution is distilled to obtain a vanillin solution. The distillation in step (A) removes impurities such as dimers and trimers of vanillin which are contained in the crude vanillin. The distillation method in the present embodiment may be, but is not limited to, simple distillation, and therefore, targeted impurities can be removed without necessity of special equipment. Preferably, the distillation is performed under reduced pressure. Here, the pressure may be appropriately set according to an aliphatic dicarboxylic acid dialkyl ester to be used, and is preferably 0.03 to 1.5 kPa, more preferably 0.1 to 0.5 kPa, in terms of a column top pressure. The temperature in the distillation may also be appropriately set according to an aliphatic dicarboxylic acid dialkyl ester to be used, and is preferably 75 to 150° C., more preferably 100 to 125° C., in terms of a column top temperature.

In the present embodiment, the crude vanillin is not particularly limited, and vanillin obtained through various known methods can be used. Specifically, crude vanillin obtained through known chemical synthetic methods and crude vanillin obtained through known biochemical methods can be used, and extracted vanillin extracted from vanilla beans can also be used. Particularly in food applications, it is preferable that natural vanillin produced through a method for producing a natural flavor as specified in U.S. Code of Federal Regulations (CFR), Vol. 21, European Parliament and Council Regulations (EC) 1334/2008, Code of Practice of International Organization of the Flavor Industry (IOFI), or the like be used as crude vanillin.

The aliphatic dicarboxylic acid dialkyl ester in the present embodiment is not particularly limited as long as it does not hinder precipitation of vanillin in anti-solvent crystallization described later, and the aliphatic dicarboxylic acid dialkyl ester is preferably one that has a boiling point close to that of vanillin, easily dissolves vanillin at room temperature, and has low reactivity with vanillin. That is, it is preferable to appropriately select the aliphatic dicarboxylic acid dialkyl ester with these criteria taken into consideration.

The boiling point of the aliphatic dicarboxylic acid dialkyl ester is preferably close to the boiling point of vanillin, which is 285° C., at 1 atm, and specifically, the boiling point of the aliphatic dicarboxylic acid dialkyl ester is preferably 265° C. or higher and 305° C. or lower. When the boiling point of the aliphatic dicarboxylic acid dialkyl ester is 265° C. or higher, it tends to be possible to prevent excessive concentration of vanillin during the later stage of distillation. When the boiling point of the aliphatic dicarboxylic acid dialkyl ester is 305° C. or lower, it tends to be possible to prevent excessive concentration of vanillin during the early stage of distillation. From the same viewpoint, the boiling point of the aliphatic dicarboxylic acid dialkyl ester is more preferably 275 to 295° C.

The solubility of vanillin in the aliphatic dicarboxylic acid dialkyl ester (25° C.) is preferably 7.5 mass % or more. When vanillin has the above-described solubility, the vanillin concentration increases in distillation, so that it tends to be possible to reduce the amount of the solvent, resulting in improvement of production efficiency. Further, the distillate liquid in distillation can be prevented from being saturated and solidified, and therefore good production efficiency can be maintained even without special equipment for resolving the solidification. From the same viewpoint, the solubility is more preferably 10 mass % or more.

For reference, Table 1 below shows the solubilities of vanillin in various solvents and the solubilities of vanillin in solvent-heptane mixed solvents (1:1) at 25° C.

TABLE 1

| Solvent | Solubility (mass %) of vanillin at 25° C. | Solubility (mass %) of vanillin in solvent-heptane mixed solvent (1:1) at 25° C. |
| --- | --- | --- |
| n-Pentadecane | 0.05% | Not measured |
| 1-Chlorotetradecane | 0.4% | Not measured |
| Isopropyl myristate | 2.0% | 0.3% |
| Ethyl laurate | 3.1% | 0.6% |
| Dibenzyl ether | 5.5% | 0.9% |
| Benzyl benzoate | 6.6% | 1.2% |
| Diisobutyl adipate | 7.7% | 1.4% |
| Dibutyl fumarate | 9.2% | 1.0% |
| Dibutyl adipate | 10.9% | 1.4% |
| Dibutyl maleate | 11.3% | 1.7% |
| Diethyl sebacate | 13.6% | 1.6% |
| Diethyl phthalate | 14.8% | Oiling out |
| Dibutyl succinate | 15.4% | 1.7% |
| γ-Undecalactone | 16.2% | 3.6% |
| δ-Decalactone | 17.4% | Oiling out |
| Tripropionin | 18.1% | Oiling out |
| Tetraglyme | 31.3% | Oiling out |

From the viewpoint described above, it is preferable to select the aliphatic dicarboxylic acid dialkyl ester in the present embodiment from the group consisting of dibutyl maleate, dibutyl succinate, diethyl sebacate, diisobutyl adipate and a mixture thereof.

Further, from the viewpoint of preventing vanillin from being excessively concentrated and precipitated due to a boiling point difference during distillation, it is preferable to use a mixture of an aliphatic dicarboxylic acid dialkyl ester having a boiling point lower than that of vanillin and an aliphatic dicarboxylic acid dialkyl ester having a boiling point higher than that of vanillin.

In the present embodiment, from the viewpoint of further suppressing precipitation of vanillin from a distillate liquid in prevention of the aforementioned solidification, it is preferable to make an adjustment so that the amount of the aliphatic dicarboxylic acid dialkyl ester used is not excessively small. From the viewpoint of further enhancing the yield of vanillin in anti-solvent crystallization as described later, it is preferable to make an adjustment so that the amount of the aliphatic dicarboxylic acid dialkyl ester used is not excessively large.

Upon adjusting the amount of the aliphatic dicarboxylic acid dialkyl ester used considering the above-described viewpoint, for example, a supersaturation ratio obtained by dividing the concentration of an extracted vanillin solution by the solubility of vanillin can be used as an index. In the present embodiment, the supersaturation ratio at 25° C. is preferably 1 or more and 2 or less, more preferably 1 or more and 1.5 or less. The value of the supersaturation ratio varies depending on the type of aliphatic dicarboxylic acid dialkyl ester used. For example, when dibutyl maleate is used, the dibutyl maleate is used in an amount of preferably 342 parts by mass (supersaturation ratio: 2) to 785 parts by mass (supersaturation ratio: 1), more preferably 490 parts by mass (supersaturation ratio: 1.5) to 785 parts by mass (supersaturation ratio: 1), based on 100 parts by mass of vanillin.

(Step (B))

In step (B), the vanillin solution obtained in step (A) is subjected to anti-solvent crystallization. The anti-solvent crystallization means a process in which a crystal is obtained by adding another solvent (poor solvent) that reduces the solubility of a solute (vanillin in the present embodiment) in a predetermined solution (vanillin solution in the present embodiment). Anti-solvent crystallization further removes impurities such as related substances to enhance the purity, so that purified vanillin can be obtained. In the present embodiment, the vanillin solution can be cooled to reduce the solubility, leading to further enhancement of the yield of the vanillin crystal (purified vanillin).

From the viewpoint of preventing an oiling out phenomenon in anti-solvent crystallization, it is preferable to use a hydrocarbon solvent as the poor solvent added. The hydrocarbon solvent is not particularly limited as long as it serves as a poor solvent in anti-solvent crystallization, and the hydrocarbon solvent is preferably one that makes the solubility of vanillin lower when mixed with a vanillin solution containing a selected aliphatic dicarboxylic acid dialkyl ester as compared to the solubility of vanillin in the aliphatic dicarboxylic acid dialkyl ester. From such a viewpoint, it is preferable to select the hydrocarbon solvent from the group consisting of n-hexane, n-heptane, cyclohexane and a mixture thereof. From the viewpoint of obtaining a vanillin crystal having better characteristics, it is more preferable to select the hydrocarbon solvent from the group consisting of n-heptane, cyclohexane and a mixture thereof. Table 1 shows the solubilities (mass %) of vanillin in solvent-heptane mixed solvents (1:1) at 25° C. with n-heptane as an example of the poor solvent. It is apparent from the table that when n-heptane is selected as a hydrocarbon solvent, it is preferable to select the aliphatic dicarboxylic acid dialkyl ester from dibutyl adipate, dibutyl maleate, diethyl sebacate and dibutyl succinate. Thus, the aliphatic dicarboxylic acid dialkyl ester and the hydrocarbon solvent in the present embodiment are selected in such a manner that the solubility of vanillin in an aliphatic dicarboxylic acid dialkyl ester-hydrocarbon solvent mixed solvent (1:1) (25° C.) is preferably 3 mass % or less, more preferably 2 mass % or less, from the viewpoint of enhancing the yield in anti-solvent crystallization.

For reference, Table 2 below shows the solubilities of vanillin in dibutyl maleate-solvent mixed solvents (1:1) at 25° C. for various solvents.

TABLE 2

| Solvent | Solubility (mass %) of vanillin in dibutyl maleate-solvent mixed solvent (1:1) at 25° C. |
| --- | --- |
| Heptane | 1.7% |
| Hexane | 1.7% |
| Petroleum ether | 1.6% |
| Isooctane | 1.8% |
| Cyclohexane | 2.1% |
| Toluene | 5.5% |

The amount of the poor solvent added in anti-solvent crystallization is preferably 50 to 300 parts by mass, more preferably 100 to 200 parts by mass, based on 100 parts by mass of the vanillin solution, from the viewpoint of the yield of vanillin and cost to use the solvent.

The temperature at which the poor solvent is added in anti-solvent crystallization depends on the type of aliphatic dicarboxylic acid dialkyl ester used and the concentration of vanillin contained, and is preferably 25 to 45° C., more preferably 30 to 40° C., from the viewpoint of controlling the particle size of purified vanillin and improving separation from the mother liquor in filtration. The method for adding the poor solvent is not particularly limited, and is preferably a method in which first an amount of the poor solvent necessary for spontaneous precipitation of a crystal is added, the mixture is stirred for 30 to 60 minutes to precipitate a crystal, and the residual amount of the poor solvent is then added. The amount necessary for spontaneous precipitation of the crystal varies depending on a combination of solvents used, and for example, when dibutyl maleate is used as the aliphatic dicarboxylic acid dialkyl ester and n-heptane is used as the poor solvent, it is preferable to add n-heptane in an amount of 10 to 40 parts by mass, more preferably 20 to 30 parts by mass, based on 100 parts by mass of the vanillin solution, and confirm precipitation of a crystal, followed by adding the residual amount of n-heptane. When cooling is performed after addition of the poor solvent, the ultimate temperature is preferably −10 to 10° C., more preferably −5 to 5° C., from the viewpoint of the yield of purified vanillin and energy necessary for cooling. From the viewpoint of further improving the yield, it is preferable that after the temperature reaches a desired temperature, the crystal be matured by performing stirring for 30 minutes or more, more preferably 60 minutes or more, while maintaining the temperature.

In the present embodiment, from the viewpoint of further improving the production efficiency of vanillin, it is preferable to further carry out the following steps: (C) separating the aliphatic dicarboxylic acid dialkyl ester and the hydrocarbon solvent from the crystallization mother liquor from step (B); and (D) recycling the aliphatic dicarboxylic acid dialkyl ester and/or the hydrocarbon solvent obtained in step (C).

(Step (C))

In step (C), by separating the aliphatic dicarboxylic acid dialkyl ester and the hydrocarbon solvent from the crystallization mother liquor in step (B), the aliphatic dicarboxylic acid dialkyl ester and the hydrocarbon solvent can be subjected to subsequent step (D). Here, the crystallization mother liquor means a solution part excluding the crystal precipitated through anti-solvent crystallization in step (B). Examples of the separation process in step (C) include, but are not limited to, distillation, and partition extraction using a solvent.

(Step (D))

In step (D), by recycling the aliphatic dicarboxylic acid dialkyl ester and/or the hydrocarbon solvent obtained in step (C), the aliphatic dicarboxylic acid dialkyl ester and the hydrocarbon solvent can be subjected to steps (A) and (B) again without being discarded. The aliphatic dicarboxylic acid dialkyl ester obtained in step (C) can be subjected to step (A), and the hydrocarbon solvent obtained in step (C) can be subjected to step (B). In step (D), a process of recycling the aliphatic dicarboxylic acid dialkyl ester to step (A) or a process of recycling the hydrocarbon solvent to step (B) may be carried out singly, and both the processes may be carried out. A process may be carried out in which impurities accompanying the aliphatic dicarboxylic acid dialkyl ester and/or the hydrocarbon solvent are removed through a conventional method before the aliphatic dicarboxylic acid dialkyl ester and/or the hydrocarbon solvent are recycled in step (D).

(Additional Purification Steps)

In the present embodiment, purified vanillin can be obtained by carrying out at least steps (A) and (B), and further carrying out steps (C) and (D) if necessary. From the viewpoint of further improving the purity, additional purification steps may be further carried out. Examples of the additional purification steps include, but are not limited to, a step of extracting a solution, which is obtained by dissolving purified vanillin in water or water-containing alcohol, with a hydrocarbon solvent to remove impurities derived from step (A) (aliphatic dicarboxylic acid dialkyl ester); and a step of further performing cooling crystallization to remove impurities (poor solvent) derived from step (B). To carry out these steps, various known purification steps can be applied.

[Composition]

A composition according to the present embodiment contains vanillin in an amount of 97.0 mass % or more and 99.99 mass % or less, an aliphatic dicarboxylic acid dialkyl ester in an amount of 0.001 mass % or more and 1 mass % or less, and a hydrocarbon solvent in an amount of 0.001 mass % or more and 1 mass % or less. The composition of the present embodiment can be favorably obtained by carrying out the method for producing vanillin according to the present embodiment described above.

From the viewpoint of quality in food applications, it is more preferable that the composition according to the present embodiment contain vanillin in an amount of 97.0 mass % or more and 99.99 mass % or less, an aliphatic dicarboxylic acid dialkyl ester in an amount of 0.001 mass % or more and 0.01 mass % or less, and a hydrocarbon solvent in an amount of 0.001 mass % or more and 0.01 mass % or less. Particularly, the composition of the present embodiment can be favorably obtained by carrying out additional purification steps in the method for producing vanillin according to the present embodiment described above.

The shape of the composition according to the present embodiment is not particularly limited, and the composition can take various forms. The composition is preferably in the form of a crystal for the sake of convenience in food applications. Here, when evaluated with a spectrophotometer, the color values of reflected light from the composition (crystal of purified vanillin) according to the present embodiment in the L*a*b* color system are preferably 88 to 96 for the L* value, −4 to +4 for the a* value and 0 to +8 for the b* value, more preferably 90 to 96 for the L* value, −3 to +3 for the a* value and 0 to +6 for the b* value. A composition satisfying the above-described color values can be favorably obtained by carrying out the method for producing vanillin according to the present embodiment.

EXAMPLES

Hereinafter, the present embodiment will be described in further detail by way of Examples, which should not be construed as limiting the present embodiment.

(Measurement of Purity)

The purities of the crude vanillin crystals used and the purified vanillin crystals obtained in Examples described below were measured in the following manner. That is, a vanillin crystal was dissolved in ethyl acetate of analytical grade, analysis was then performed by gas chromatography (GC), and the ratio of the peak area value of vanillin to the total value of all peak areas except for peaks derived from ethyl acetate in a chromatogram obtained was defined as a purity. The analysis conditions were as follows.

Apparatus: Agilent GC6850N
Column: HP-1 (manufactured by Agilent Technologies, Inc.), 30 m×0.25 mm×0.25 µm
Carrier gas: Nitrogen, 0.7 mL/min
Oven temperature: held at 100° C. for 4 minutes, then heated at 10° C./min and held at 300° C. for 16 minutes
Inlet: 300° C., sprit ratio=100:1
Detector: FID detector, 300° C.

Example 1-1

10.0 g of prepared crude vanillin (extracted concentrate of a culture solution obtained by fermentation; purity: 92.8%; color values measured by a spectrophotometer (SE7700 manufactured by Nippon Denshoku Industries Co., Ltd.): L*=67.8, a*=2.4 and b*=43.2) and 50.0 g of dibutyl maleate were introduced into a distillation apparatus assembled from a two-necked flask having a volume of 100 mL, a thermometer, a distillation head, a Liebig condenser and a Perkin triangle, and reduced-pressure distillation was performed at 0.5 kPa. A forerunning distillate fraction with a weight of 1.2 g (column top temperature: 126° C. or lower) was discharged to outside the system, followed by obtaining a main distillate fraction with a weight of 57.5 g (column top temperature: 126° C.). On the other hand, 0.4 g of a brown solid was obtained as a distilled residue. Even when the main distillate fraction was left standing at 25° C. for 16 hours, no crystal was precipitated. 56.7 g of the obtained main distillate fraction was transferred into a 300 mL round-bottomed flask, and held at 30° C. in a hot water bath while being stirred with a magnetic stirrer. To this was added 15.0 g of n-heptane, and the mixture was stirred for 30 minutes to precipitate a crystal. 45.0 g of n-heptane was further added, and the mixture was stirred for 30 minutes, then transferred into an ice bath to be cooled to 4° C., and stirred at this temperature for 1 hour to completely precipitate a crystal. The thus-obtained slurry containing a crystal was subjected to suction filtration by a diaphragm pump with a Buchner funnel to separate the slurry into a crystal and a mother liquor, and the crystal was rinsed with 20.0 g of n-heptane twice to remove the mother liquor, and then dried under reduced pressure to obtain 7.5 g of a white purified vanillin crystal. The purified vanillin crystal had a purity of 98.8%, and contained 0.6% of n-heptane and 0.2% of dibutyl maleate as residual solvents. The obtained purified crystal was evaluated using a spectrophotometer, and the result showed that the color values were 90.8 for L*, −2.7 for a* and 7.6 for b*.

Thus, it was shown that by the method for producing vanillin according to the present embodiment, a purified vanillin crystal having a high purity and good characteristics was obtained with industrially sufficient efficiency without use of a special apparatus.

Example 1-2

The mother liquor obtained in Example 1 was analyzed by GC, and the result showed that the mother liquor had a composition of n-heptane: 88.6%, vanillin: 0.3% and dibutyl maleate: 10.7%. 144.6 g of the mother liquor was introduced into a distillation apparatus assembled from a four-necked flask having a volume of 300 mL, a thermometer, a distillation head, a Liebig condenser and a Perkin triangle, and distilled at 1 atm. Extraction was performed until the residue temperature became 130° C., and 83.1 g of recovered n-heptane (purity: 99.8%) and 60.9 g of a residue (GC composition: heptane: 88.6%, vanillin: 0.3% and dibutyl maleate: 10.7%) were obtained as distillate liquids. The residue was cooled, then decompressed to 3.5 kPa, and heated to 50° C. to distill off remaining n-heptane (not recovered), thereby obtaining 49.5 g of recovered dibutyl maleate (purity: 93.2%, vanillin: 3.6% and residual n-heptane: 0.6%).

Thus, it was shown that carrying out step (C) in the present embodiment enabled recovery and reuse of much dibutyl maleate and n-heptane.

Example 1-3

The following purification was performed to further enhance the purity of purified vanillin. First, 7.3 g of the purified vanillin crystal obtained in Example 1 was introduced into a two-necked flask equipped with a thermometer and having a volume of 100 mL, and 7.3 g of water and 36.3 g of n-heptane were added, the mixture was heated in a water bath at 65° C. and stirred for 30 minutes to dissolve a crystal, so that impurities contained in the crystal were extracted into the n-heptane. The n-heptane phase was removed while this temperature was maintained. To the resulting aqueous phase was added 36.3 g of n-heptane again, and the mixture was heated in a water bath at 65° C. and stirred for 30 minutes to perform extraction again. To the obtained aqueous phase were added 7.3 g of ethanol and 50.9 g of water, and the mixture was heated to 60° C., then slowly cooled to 5° C., and stirred at this temperature for 1 hour to completely precipitate a crystal. The thus-obtained slurry containing a crystal was subjected to suction filtration by a diaphragm pump with a Buchner funnel to separate the slurry into a crystal and a mother liquor, and the crystal was rinsed with 3.0 g of water twice to remove the mother liquor, and then dried with a desiccator under reduced pressure to obtain 7.1 g of a white purified vanillin crystal. The purified crystal had a purity of 99.9%, and contained 0.02% of n-heptane and 0.005% of dibutyl maleate as residual solvents. The color values were 94.7 for $L^*$, −1.7 for $a^*$ and 5.0 for $b^*$.

Thus, it was shown that by adding purification steps in the method for producing vanillin according to the present embodiment, a purified vanillin crystal having a higher purity and good characteristics was obtained with industrially sufficient efficiency without use of a special apparatus.

Example 2

10.0 g of the crude vanillin used in Example 1 and 60.0 g of dibutyl adipate were introduced into a distillation apparatus assembled from a four-necked flask having a volume of 200 mL, a thermometer, a distillation head, a Liebig condenser and a Perkin triangle, and reduced-pressure distillation was performed at 0.1 kPa. A forerunning distillate fraction with a weight of 1.8 g (column top temperature: 104° C. or lower) was discharged to outside the system, followed by obtaining a main distillate fraction with a weight of 66.9 g (column top temperature: 104° C.). On the other hand, 0.7 g of a brown solid was obtained as a distilled residue. Even when the main distillate fraction was left standing at 25° C. for 16 hours, a crystal was not precipitated. 66.5 g of the obtained main distillate fraction was transferred into a 300 mL round-bottomed flask, and held at 30° C. in a hot water bath while being stirred with a magnetic stirrer. To this was added 45.0 g of cyclohexane, and the mixture was stirred for 30 minutes to precipitate a crystal. 45.0 g of cyclohexane was further added, and the mixture was stirred for 30 minutes, then transferred into an ice bath to be cooled to 4° C., and stirred at this temperature for 1 hour to completely precipitate a crystal. The thus-obtained slurry containing a crystal was subjected to suction filtration by a diaphragm pump with a Buchner funnel to separate the slurry into a crystal and a mother liquor, and the crystal was rinsed with 20.0 g of cyclohexane twice to remove the mother liquor, and then dried under reduced pressure to obtain 6.4 g of a white purified vanillin crystal. The purified vanillin crystal had a purity of 97.7%, and contained 0.4% of cyclohexane and 1.9% of dibutyl adipate as residual solvents. The obtained purified crystal was evaluated using a spectrophotometer, and the result showed that the color values were 89.1 for $L^*$, −1.5 for $a^*$ and 2.3 for $b^*$.

Thus, it was shown that even when the types of the aliphatic dicarboxylic acid dialkyl ester and the hydrocarbon solvent were changed, a purified vanillin crystal having a higher purity and good characteristics was obtained with industrially sufficient efficiency without use of a special apparatus.

Example 3

In accordance with U.S. Pat. No. 4,163,759, Example 3, vanillin was prepared using 29.6 g (0.20 mol) of a 50 mass % aqueous solution of glyoxylic acid and 31.0 g (0.25 mol) of guaiacol as starting materials. The solvent was removed from a toluene extract of the reaction mixture under reduced pressure to obtain 22.4 g of a red-brown crystal of crude vanillin (GC composition: toluene: 3.3%, guaiacol: 16.1% and vanillin: 80.5%, color values: $L^*=42.4$, $a^*=-10.1$ and $b^*=19.6$).

The crude vanillin obtained as described above and dibutyl maleate (90.2 g) were introduced into a distillation apparatus assembled from a three-necked flask having a volume of 200 mL, a thermometer, a distillation head, a Liebig condenser and a Perkin triangle, and reduced-pressure distillation was performed at 0.2 kPa. The distillate was not fractionated, and 105.7 g of a light yellow distillate liquid was obtained at a column top temperature of 63 to 111° C. On the other hand, 4.9 g of a brown solid was obtained as a distilled residue. Even when the main distillate fraction was left standing at 25° C. for 16 hours, a crystal was not precipitated. The total amount of the obtained main distillate fraction was transferred into a 500 mL round-bottomed flask, and held at 30° C. in a hot water bath while being stirred with a magnetic stirrer. To this was added 27.0 g of n-heptane, and the mixture was stirred for 30 minutes to precipitate a crystal. 81.0 g of n-heptane was further added, and the mixture was stirred for 30 minutes, then transferred into an ice bath to be cooled to 4° C., and stirred at this temperature for 1 hour to completely precipitate a crystal. The thus-obtained slurry containing a crystal was subjected to suction filtration by a diaphragm pump with a Buchner funnel to separate the slurry into a crystal and a mother liquor, and the crystal was rinsed with 36.0 g of n-heptane twice to remove the mother liquor, and then dried under reduced pressure to obtain 12.8 g of a white purified vanillin crystal. The purified crystal had a purity of 99.3%, and contained 0.07% of guaiacol as an impurity and 0.1% of n-heptane and 0.4% of dibutyl maleate as residual solvents. The obtained purified crystal was evaluated using a spectrophotometer, and the result showed that the color values were 94.4 for $L^*$, −0.8 for $a^*$ and 1.6 for $b^*$.

Thus, it was shown that by the method for producing vanillin according to the present embodiment, a purified vanillin crystal having a high purity and good characteristics was obtained with industrially sufficient efficiency without use of a special apparatus even when synthesized crude vanillin was used.

Comparative Example 1

10.0 g of the crude vanillin used in Example 1 and 90.0 g of dibenzyl ether were introduced into a distillation apparatus assembled from a four-necked flask having a volume of 200 mL, a thermometer, a distillation head, a Liebig condenser and a Perkin triangle, and reduced-pressure distillation was performed at 0.1 kPa. Extraction was started at a column top temperature of 111° C.; however, because vanillin in the early distillate liquid was supersaturated, a crystal was immediately precipitated in the Liebig condenser, so that the flow channel was blocked. Thus, it was impossible to continue distillation.

Comparative Example 2

10.0 g of the crude vanillin used in Example 1 and 50.0 g of diethyl phthalate were introduced into a distillation apparatus assembled from a two-necked flask having a volume of 100 mL, a thermometer, a distillation head, a Liebig condenser and a Perkin triangle, and reduced-pressure distillation was performed at 0.1 kPa. A forerunning distillate fraction with a weight of 1.2 g (column top temperature: 108° C. or lower) was cut, followed by obtaining a main distillate fraction with a weight of 57.8 g (column top temperature: 108° C.). 0.4 g of a brown solid was obtained as a distilled residue. Even when the main distillate fraction was left standing at 25° C. for 16 hours, a crystal was not precipitated. 56.6 g of the obtained main distillate fraction was transferred into a 300 mL round-bottomed flask, and held at 30° C. while being stirred with a magnetic stirrer. To this was added 100.0 g of n-heptane to try crystallization, and because presence of vanillin reduced the solubility of n-heptane in diethyl phthalate, phase separation of the n-heptane occurred, so that it was not possible to precipitate vanillin.

The present application claims a priority from the Japanese patent application filed with the Japan Patent Office on Feb. 9, 2018 (Japanese Patent Application No. 2018-022271), the disclosure of which is incorporated herein by reference.

The invention claimed is:

1. A method for producing vanillin, comprising the steps of:
   (A) distilling a solution comprising crude vanillin and an aliphatic dicarboxylic acid dialkyl ester to obtain a vanillin solution; and
   (B) subjecting the vanillin solution to anti-solvent crystallization.

2. The method for producing vanillin according to claim 1, wherein a hydrocarbon solvent is used in the anti-solvent crystallization.

3. The method for producing vanillin according to claim 1, wherein the aliphatic dicarboxylic acid dialkyl ester is selected from the group consisting of dibutyl maleate, dibutyl succinate, diethyl sebacate, diisobutyl adipate and a mixture thereof.

4. The method for producing vanillin according to claim 2, wherein the hydrocarbon solvent is selected from the group consisting of n-hexane, n-heptane, cyclohexane and a mixture thereof.

5. The method for producing vanillin according to claim 2, further comprising the following steps:
   (C) separating the aliphatic dicarboxylic acid dialkyl ester and the hydrocarbon solvent from a crystallization mother liquor from step (B); and
   (D) recycling the aliphatic dicarboxylic acid dialkyl ester and/or the hydrocarbon solvent obtained in step (C).

6. A composition comprising:
   vanillin in an amount of 97.0 mass % or more and 99.99 mass % or less;
   an aliphatic dicarboxylic acid dialkyl ester in an amount of 0.001 mass % or more and 1 mass % or less; and
   a hydrocarbon solvent in an amount of 0.001 mass % or more and 1 mass % or less.

* * * * *